United States Patent

Edwards et al.

[11] Patent Number: 5,559,096
[45] Date of Patent: Sep. 24, 1996

[54] PHARMACEUTICAL COMPOSITIONS AGAINST GASTRIC DISORDERS

[75] Inventors: Peter J. Edwards; Kim Morwood, both of Weybridge, United Kingdom

[73] Assignee: Applied Microbiology, Inc., Brooklyn, N.Y.

[21] Appl. No.: 129,134

[22] PCT Filed: Apr. 10, 1992

[86] PCT No.: PCT/GB92/00656

§ 371 Date: Dec. 14, 1993

§ 102(e) Date: Dec. 14, 1993

[87] PCT Pub. No.: WO92/18143

PCT Pub. Date: Oct. 29, 1992

[30] Foreign Application Priority Data

Apr. 15, 1991 [GB] United Kingdom ............ 9108129
Jul. 1, 1991 [GB] United Kingdom ............ 9114149

[51] Int. Cl.⁶ .................. A61K 38/00; A61K 31/14

[52] U.S. Cl. .................. 514/12; 514/2; 514/9; 514/11

[58] Field of Search .................. 514/2, 9, 11, 12

[56] References Cited

U.S. PATENT DOCUMENTS

| 4,615,697 | 10/1986 | Robinson | 604/890 |
| 4,980,163 | 12/1990 | Blackburn et al. | 514/12 |
| 5,304,540 | 4/1994 | Blackburn et al. | 514/2 |
| 5,334,582 | 8/1994 | Blackburn et al. | 514/2 |

*Primary Examiner*—Elizabeth C. Weimar
*Assistant Examiner*—P. Lynn Touzeau
*Attorney, Agent, or Firm*—White & Case

[57] ABSTRACT

The invention concerns pharmaceutical compositions for use in the treatment of gastric disorders associated with *Helicobacter pylori* comprising a bacteriocin antimicrobial agent optionally coadministered with a release-delaying substance.

2 Claims, No Drawings

PHARMACEUTICAL COMPOSITIONS AGAINST GASTRIC DISORDERS

The present invention relates to pharmaceutical compositions of antimicrobial agents active against *Helicobacter pylori* and their use in the treatment of gastrointestinal disorders associated with *Helicobacter pylori* infection.

*Helicobacter pylori* (formerly known as *Campylobacter pyloridis*) is a spiral-shaped Gram-negative organism which appears to live beneath the mucus layer of the stomach. Many recent studies have shown an association between the presence of *H. pylori* in the gastric mucosa and histologically confirmed gastritis.

In the light of these results, it has been suggested that the organism may be a pathogen which causes, or at least exacerbates, gastritis, and may also be important in the aetiology of peptic triceration. Reviews on the state of the art include those by C.A.M. McNulty in *J. Infection*, 1986, 13, 107–113, and by C. S. Goodwin et al. in *J. Clin. Pathol.*, 1986, 39, 353–365.

*H.pylori* is known to be susceptible to a large number of antimicrobial agents in vitro. Furthermore, several workers have shown that treatment of gastritis with antimicrobial agents, for example β-lactam antibiotics such as amoxycillin, or bismuth salts, leads to eradication of the associated *H.pylori* organism in vivo.

Bacteriocins are peptide antimicrobial agents defined as proteinaceous substances produced by bacteria which have antimicrobial activity only against species closely related to the species of origin.

An example of a bacteriocin which has found commercial application is nisin. Nisin is a lanthocin comprising the atypical amino acid lanthionine. Nisin is a polypeptide having antibacterial properties which is produced naturally by various strains of the bacterium *Streptococcus lactis*. It is found at low concentration in milk and cheese. It is used as a food preservative to inhibit the outgrowth of spores of certain species of Gram positive bacteria. See U.S. Pat. Nos. 5,584,199 and 4,597,972 (Taylor). Nisin is recognised by the FDA as a direct food ingredient. It is considered non-toxic and non-allergenic to humans and, as a proteinaceous material, any residues in ingested foods are quickly degraded by digestive enzymes. A summary of nisin's properties is to be found in Advances in Applied Microbiology, 27, 85–123, (1981).

Recently, a purified form of nisin has been made available by Applied Microbiology Inc. under the trade name AMBICIN N. It has been suggested for use in a variety of applications, for example for use in oral care.

Nisin, in common with other bacteriocin antimicrobial agents, is generally regarded as ineffective against Gram negative bacteria, other than in the presence of non-bacterial enhancers such as chelating agents and surfactants. See PCT Publication No. WO 89/12399 (Blackburn).

Surprisingly, it has now been found that the group of bacteriocin peptide antimicrobial agents is efficacious in the in vitro eradication of the Gram negative organism *Helicobacter pylori* and therefore has potential utility in the treatment of *H.pylori* mediated gastric disorders in mammals.

Accordingly, the present invention provides the use of a bacteriocin antimicrobial agent for the manufacture of a medicament for the treatment of gastric disorders associated with *H.pylori*.

Suitable bacteriocin antimicrobial agents include nisin, gramicidin and tyrothricin including derivatives and purified forms of bacteriocins such as Ambicin N.

The invention also includes a method of treatment of gastric disorders associated with *Helicobacter pylori* in mammals which method comprises the administration to a mammal in need of treatment of an effective amount of a bacteriocin antimicrobial agent.

A pharmaceutical composition for use in the treatment of gastric disorders associated with *Helicobacter pylori*, comprising a bacteriocin antimicrobial agent and a pharmaceutically acceptable carrier also forms part of the present invention.

It has been found that treatment of *H. pylori* associated gastritis with antimicrobial agents given by a conventional oral dosing regimen may require a prolonged course of therapy to be effective. Furthermore, follow-up of patients cleared of *H.pylori* infection by antimicrobial treatment has shown that relapse (rather than reinfection) can be a problem.

In another aspect of the invention, substances having activity against *H. pylori* may be formulated as gastric controlled release compositions, more especially as compositions which prolong residence time of the antimicrobial agent within the stomach.

Bioadhesive materials have received considerable attention as platforms for controlled drug deliver. They can be targetted, to specific drug administration sites, prolong the residence time and ensure an optimal contact with the absorbing surface. Many different types of bioadhesive materials, both natural and synthetic, can be used in the design of controlled drug delivery systems.

Sucralfate, a basic aluminium sulphate sucrose complex, is an ulcer-preventing agent having anti-pepsin and antiadd properties. It has gastric muco-adherent properties such that when administered orally it reacts with gastric juice to form a sticky paste which protects the mucosa by coating, and also binds to ulcer-affected sites. The preparation and use of sucralfate is described in for example U. S. Pat. No. 3432489 and "The Merck Index" 11th edition (1989) p1400 entry No 8853.

EP-A-0 403 048 (Warner-Lambert) describes medicated compositions comprising sucralfate and a therapeutically effective amount of a medicament which is a) substantially water insoluble, or b) a mixture of a water-soluble medicament and a release-delaying material which on admixture forms a substantially water-insoluble medicament. The specification identifies gastro-unstable medicaments, including peptides, as suitable compounds for formulation with sucralfate. Gastro-unstable medicaments are defined in EP-A 0 403 048 as compounds which are degraded in the gastric fluids of the stomach. Surprisingly, bacteriocin peptide antimicrobial agents have been found to remain stable under the acid conditions prevailing in the stomach; they do not therefore fall within the class of gastro-unstable peptides as defined by Warner-Lambert.

U.S. Pat. No. 4,615 697 (Robinson et al.) discloses a controlled release composition comprising an effective amount of a treating agent, which may be a medicament, and a bioadhesive material which is a water-swellable and water-insoluble, fibrous, cross-linked carboxy-functional polymer. The controlled release compositions are described as adhering to the skin or the mucous membranes in the presence of water.

In a further aspect, the present invention relies on the co-formulation or co-administration of a bacteriocin antimicrobial agent which is active against *Helicobacter pylori* with one or more substances capable of providing a controlled release of the antimicrobial agent in the stomach. In particular, the present invention relies on the incorporation of a bacteriocin antimicrobial agent which is active against *H.pylori* into the sticky paste formed by a muco adherent, for example sucralfate, in situ, providing a sustained release or prolonged retention of the antimicrobial agent in the stomach, so as to overcome, or at least mitigate, the disadvantages associated with conventionally formulated antimicrobial agents and provide an effective treatment for *H.pylori* infections of the gastric and duodenal mucosa in humans and domestic animals.

Accordingly, the present invention provides pharmaceutical compositions comprising one or more bacteriocin antimicrobial agents effective against *H. pylori* organisms, and one or more substances providing a sustained release and/or prolonged retention of the bacteriocin antimicrobial agent in the stomach.

The present invention extends to these compositions for use in therapy and to the use of these compositions in the manufacture of a medicament for the treatment of gastric disorders associated with *Helicobacter pylori*.

The antimicrobial agent may for example be co-formulated, suitably by intimate admixture, with a muco-adherent or bioadhesive substance to form a bioadhesive complex. Such a complex confers the additional benefit of locally targetting the antimicrobial agent to the mucus layer of the stomach wall.

Bioadhesive materials suitable for use in compositions of the present invention include materials, both natural and synthetic, which are capable of adhering to biological surfaces such as mucus membranes. Examples of bioadhesive materials include natural gums and plant extracts and synthetic materials such as sucralfate, cellulose derivatives, acrylic acid and methacrylic acid derivatives, for example cross-linked acrylic and methacrylic acid copolymers available under the Trade Names CARBOPOL and POLYCARBOPHIL.

Antimicrobial agents effective against *H. pylori* may alternatively be formulated to produce a floating alginate raft within the stomach. Such formulations may include solid and liquid dosage forms, and may be prepared according to processes known to persons skilled in the art.

Controlled release dosage forms, for example beadlets or granules, optionally encapsulated or compressed to form tablets, also form part of the invention. Advantageously, beadlets or granules are coated, layered, or form an intimate, homogeneous matrix with release-delaying materials. Such dosage forms may be prepared using conventional techniques known in the art.

The bacteriocin antimicrobial agent is present in compositions of the invention in an appropriate amount to provide an effective dose, which will depend on the pharmacological properties of the antimicrobial agent employed. Normally a single dose used to treat an adult human will provide up to 20 g, generally 0.5 to 4.0 g of antimicrobial agent.

Suitably the composition of the invention comprises from 0.1 to 5 parts by weight of antimicrobial agent per part by weight of bioadhesive agent or muco-adherent, more preferably from 0.5 to 1 part of antimicrobial agent per part of bioadhesive agent or muco-adherent, for example of sulfacrate.

A composition of the present invention may also include additional therapeutic agents useful in the treatment of peptic ulcers and gastritis, and agents which delay gastric emptying, for example methylcellulose, guar gum, fats such as triglyceride esters, and triethanolamine myristate.

A composition of the invention may be made up in the form of a swallow tablet, a chewable tablet or a water dispersible tablet. Alternatively it may be supplied as a water-dispersible powder, either for dispersion immediately prior to administration or for dispensing in liquid form, as a suspension or as a liquid emulsion. Suitable water-dispersible formulations include soluble effervescent or non-effervescent powders.

The compositions of the present invention may also contain appropriate additives, for example preservatives, buffering agents, suspending agents, flavorings, bulking agents, binders, adhesives, lubricants, disintegrants, colouring agents, sweeteners, adsorbents, thickeners, suspending agents, and diluents including water, appropriate to their form.

Coatings able to retard the release of pharmaceuticals are well known in the art of pharmaceutical formulation, and include polymers such as acrylic resins (for example the material sold by Rohm Pharma under the trade name 'Eudragit') and cellulose esters (for example ethyl cellulose). If desired, the release of the antimicrobial agent may be altered by changing the particle size of a coated or encapsulated antimicrobial agent.

An encapsulated or delayed release formulation according to the invention may be any such form well known in the art. Suitable coating materials include water-based coatings, solvent-based coatings and colloidal dispersions. Lipids may also be used to form liposome-type formulations.

It has also been found that the activity of bacteriocin antimicrobial agents active against *Helicobacter pylori* may be enhanced if these agents are administered in combination with various materials which are not recognised as antimicrobial agents per se, for example chelating agents, surfactants and mixtures thereof.

Accordingly, bacteriocin antimicrobial agents and compositions containing bacteriocin antimicrobial agents as hereinbefore described for use in the treatment of *Helicobacter pylori*, further comprising a chelating agent, a surfactant or mixtures thereof also form part of the invention.

Suitable chelating agents include alkyldiamine tetraacetates, for example ethylenediaminetetraacetic acid (EDTA), CaEDTA, and CaNa$_2$EDTA, EGTA and citrate.

Suitable surfactants include ionic and non-ionic surfactants. Examples of non-ionic surfactants include glycerides and the materials commercially available under the Trade Names Tweens and Tritons. Ionic surfactants include fatty acids and quaternary compounds, the anionic surfactant sodium dodecyl sulphate, and amphoteric surfactants such as cocamidopropyl betaine and emulsifiers.

A composition of the invention may be administered as often as a physician directs, having regard to the severity of the *H.pylori* infection. Normally, it is recommended to take a dose two or three times daily, advantageously after meals.

Compositions of the invention may be prepared by conventional pharmaceutical techniques. Thus compositions may, for example, be prepared by mixing together the required ingredients with stirring or grinding to ensure adequate dispersion. Alternatively, some of the ingredients may be mixed together before other ingredients are added. Granulation and/or coating techniques may be used at a convenient stage in the process if required.

The invention will now be illustrated by the following examples.

EXAMPLE 1

Activity of Bacteriocin Antimicrobial Agents against *Helicobacter Pylori*

The Minimum Inhibitory Concentration (MIC) of bacteriocin antimicrobial agents against a human strains of *H.pylori* (*H.pylori* NCTC 11916 and NCTC 11637) were assessed using a spiral plater and automatic agar plate pourer, according to the method of Wallace A. S. and Corkill J. E. (J. Microbial. Methods, 10, 303–310, 1989). MIC values were calculated according to the equation for the Archimedes spiral.

Kill time was calculated as the time taken to reduce microbe levels to <200 viable organisms using a drug concentration equal to 4 times the average MIC value for the test compound.

|  | MIC Value (mg/l) | | |
|---|---|---|---|
| Compound | NCTC 11916 | NCTC 11637 | Kill Time |
| Tyrothricin | 1.0–4.0 | 1.0–5.0 | <1 |
| Gramicidin | 0.5–3.0 | 1.0–3.5 | >30 |
| Ambicin N | 50–300 | 50–300 | >30 |

EXAMPLE 2

Effect of Chelating Agent on activity of Bacteriocin Antimicrobial Agents against *Helicobacter Pylori*

A kill time assay was carried out to determine the effect of citrate on antimicrobial activity. Microbe survival was assessed after treatment with bacteriocin alone and bacteriocin plus citrate. The effect of citrate alone was also measured. Survival was measured at 1,5 and 30 minutes after inoculation. Activity is expressed as the mean number of counts of colony forming units (CFU) per ml.

|  | Mean Counts CFU/ml | | |
|---|---|---|---|
| Compound | 1 min | 5 min | 30 min |
| Citrate (10 mM) | $7.98 \times 10^4$ | $8.64 \times 10^4$ | $6.92 \times 10^4$ |
| Ambicin N (300 ppm) | $6.31 \times 10^4$ | $5.71 \times 10^4$ | $4.72 \times 10^4$ |
| Ambicin/Citrate (Initial Inoculum = $8.92 \times 10^4$) | $8.42 \times 10^4$ | $5.87 \times 10^4$ | $2.94 \times 10^4$ |
| Citrate (10 mM) | $1.59 \times 10^4$ | $1.42 \times 10^4$ | $1.95 \times 10^4$ |
| Gramicidin | $7.69 \times 10^3$ | $1.44 \times 10^4$ | $1.35 \times 10^4$ |
| Gramicidin/Citrate (Initial Inoculum = $2.39 \times 10^5$) | $1.17 \times 10^3$ | $1.39 \times 10^3$ | $1.71 \times 10^3$ |
| Citrate (10 mM) | $1.59 \times 10^4$ | $1.42 \times 10^4$ | $1.95 \times 10^4$ |
| Tyrothricin | $2.55 \times 10^4$ | $1.77 \times 10^4$ | $1.78 \times 10^4$ |
| Tyrothricin/Citrate (Initial Inoculum = $2.39 \times 10^5$) | $1.08 \times 10^4$ | $7.94 \times 10^3$ | $1.74 \times 10^4$ |

EXAMPLE 3

| Formulation Examples | | mg. |
|---|---|---|
| i) Gramicidin | | 500 |
| Sucralfate | | 500 |
| Carboxymethyl sodium starch glycollate, (dried) | | 30 |
| Magnesium stearate | | 20 |
| Silica | | 12 |
| Microcrystalline Cellulose | to | 1500 |
| ii) Ambicin N | | 500 |
| Sucralfate | | 500 |
| Carboxymethyl sodium starch glycollate, (dried) | | 30 |
| Magnesium stearate | | 20 |
| Silica | | 12 |
| Microcrystalline Cellulose | to | 1500 |

Method:

All the ingredients except for one third of the magnesium stearate are screened, blended, and compressed on a rotary tabletting machine to fore slugs. The slugs are milled, blended with the remaining magnesium stearate, and recompressed to fore the final tablets.

iii) A tablet was prepared according to standard methods including tyrothridn (500 mg) and encapsulated with POLYCARBOPHIL.

iv) A tablet was prepared according to standard methods including nisin (500 mg) and alginate (1 g).

v) An effervescent powder was prepared containing per 5 g dose:

| tyrothricin: | 500 mg |
|---|---|
| citric acid (anhydrous): | 2.2 g |
| sodium bicarbonate: | 2.3 g |
| sodium carbonate: | 0.5 g |

We claim:

1. A pharmaceutical composition comprising a bacteriocin antimicrobial agent selected from the group consisting of nisin, gramicidin, tyrothricin and analogs thereof in combination with a mucoadherent or bioadhesive release-sustaining agent which is a natural gum, a plant extract, sucralfate, a cellulose derivative or an acrylic acid or methacrylic acid derivative in a pharmaceutically acceptable carrier.

2. A method of treating gastric disorders associated with *Helicobacter pylori* in mammals which comprises administering to a mammal in need of such treatment a pharmaceutical composition according to claim 1 comprising an amount of the bacteriocin antimicrobial agent effective to treat the disorder.

* * * * *